United States Patent
Bruch-El et al.

(10) Patent No.: US 12,211,208 B2
(45) Date of Patent: Jan. 28, 2025

(54) AUTOMATED ANALYSIS OF IMAGE DATA TO DETERMINE FRACTIONAL FLOW RESERVE

(71) Applicant: MEDHUB LTD, Tel Aviv (IL)

(72) Inventors: Or Bruch-El, Tel Aviv (IL); David Goldman, Nesher (IL); Alexandre Kassel, Tel Aviv (IL)

(73) Assignee: MEDHUB LTD, Tel Aviv (IL)

( * ) Notice: Subject to any disclaimer, the term of this patent is extended or adjusted under 35 U.S.C. 154(b) by 308 days.

(21) Appl. No.: 17/641,126

(22) PCT Filed: Sep. 7, 2020

(86) PCT No.: PCT/IL2020/050973
§ 371 (c)(1),
(2) Date: Mar. 8, 2022

(87) PCT Pub. No.: WO2021/048838
PCT Pub. Date: Mar. 18, 2021

(65) Prior Publication Data
US 2022/0335612 A1    Oct. 20, 2022

Related U.S. Application Data

(60) Provisional application No. 62/897,453, filed on Sep. 9, 2019.

(30) Foreign Application Priority Data

Sep. 9, 2019  (IL) .......................................... 269223

(51) Int. Cl.
*G06T 7/00*  (2017.01)
*A61B 5/00*  (2006.01)
*A61B 5/02*  (2006.01)

(52) U.S. Cl.
CPC ........ *G06T 7/0014* (2013.01); *A61B 5/02007* (2013.01); *A61B 5/02028* (2013.01);
(Continued)

(58) Field of Classification Search
CPC ............... G06T 7/0014; G06T 2200/24; G06T 2207/30048; G06T 2207/30104;
(Continued)

(56) References Cited

U.S. PATENT DOCUMENTS 9,700,219 B2  7/2017  Sharma et al.
9,814,433 B2  11/2017  Benishti et al.
(Continued)

FOREIGN PATENT DOCUMENTS

EP    3277183 B1    2/2018
JP    H08131429 A   5/1996
(Continued)

OTHER PUBLICATIONS

Cong et al. Automated Stenosis Detection and Classification in X-ray Angiography Using Deep Neural Network, IEEE International Conference on Bioinformatics and Biomedicine, Nov. 21, 2019. pp. 1301-1308, BIBM 2019.

*Primary Examiner* — Khai M Nguyen
(74) *Attorney, Agent, or Firm* — AlphaPatent Associates Ltd.; Daniel J. Swirsky (57) ABSTRACT

A system and method for analysis of a vessel automatically detects a pathology in a first image of the vessel and attaches a virtual mark to the pathology in the first image. The system may detect the same pathology in a second image of the vessel, based on the virtual mark, and may then provide analysis (e.g., determine an FFR value) of the pathology based on the pathology detected in the first and second images.

16 Claims, 9 Drawing Sheets

(52) U.S. Cl.
CPC .......... *A61B 5/743* (2013.01); *G06T 2200/24* (2013.01); *G06T 2207/30048* (2013.01); *G06T 2207/30104* (2013.01); *G06T 2207/30204* (2013.01)

(58) Field of Classification Search
CPC ...... G06T 2207/30204; A61B 5/02007; A61B 5/02028; A61B 5/743
See application file for complete search history.

(56) References Cited

U.S. PATENT DOCUMENTS

| | | | |
|---|---|---|---|
| 9,891,044 | B2 | 2/2018 | Tu et al. |
| 10,111,633 | B2 | 10/2018 | Nickisch et al. |
| 10,210,956 | B2 | 2/2019 | Lavi et al. |
| 10,219,704 | B2 | 3/2019 | Lavi et al. |
| 10,229,516 | B2 | 3/2019 | Aben et al. |
| 10,235,796 | B2 | 3/2019 | Aben et al. |
| 10,262,101 | B2 | 3/2019 | Aben et al. |
| 10,360,674 | B2 | 7/2019 | Contini et al. |
| 10,376,165 | B2 * | 8/2019 | Lavi ................ A61B 5/107 |
| 10,395,366 | B2 * | 8/2019 | Isgum ............ G06F 18/2411 |
| 11,813,099 | B2 | 11/2023 | Anderson et al. |
| 2014/0121513 | A1 | 5/2014 | Tolkowsky et al. |
| 2014/0200867 | A1 | 7/2014 | Avi et al. |
| 2014/0249417 | A1 | 9/2014 | Ookouchi et al. |
| 2016/0022371 | A1 | 1/2016 | Sauer et al. |
| 2016/0148372 | A1 | 5/2016 | Itu et al. |
| 2016/0157807 | A1 | 6/2016 | Anderson et al. |
| 2017/0245822 | A1 | 8/2017 | Vaillant et al. |
| 2017/0311821 | A1 | 11/2017 | Ledoux et al. |
| 2018/0330507 | A1 | 11/2018 | Schormans et al. |
| 2019/0000055 | A1 | 1/2019 | Taylor et al. |
| 2019/0038356 | A1 | 2/2019 | Schmitt et al. |
| 2019/0095574 | A1 | 3/2019 | Taylor et al. |
| 2019/0156554 | A1 | 5/2019 | Aben et al. |
| 2019/0159737 | A1 * | 5/2019 | Buckler ............ A61B 6/5217 |
| 2019/0164649 | A1 | 5/2019 | Lavi et al. |
| 2019/0172197 | A1 * | 6/2019 | Buckler ............... G06F 18/24 |
| 2019/0180153 | A1 | 6/2019 | Buckler et al. |
| 2019/0192012 | A1 | 6/2019 | Lavi et al. |
| 2020/0129148 | A1 | 4/2020 | Jenkins et al. |
| 2021/0110533 | A1 | 4/2021 | Viti et al. |
| 2023/0306596 | A1 * | 9/2023 | Choi .................... G16H 50/20 |

FOREIGN PATENT DOCUMENTS

| | | |
|---|---|---|
| JP | 2015527901 A | 9/2015 |
| WO | 2015059706 A2 | 4/2015 |
| WO | 2017200381 A1 | 11/2017 |

* cited by examiner

AUTOMATED ANALYSIS OF IMAGE DATA TO DETERMINE FRACTIONAL FLOW RESERVE

FIELD

The present invention relates to automated vessel analysis from image data, including automatic determination of functional measurements, such as fractional flow reserve, and to interfacing the analysis to a user.

BACKGROUND

Artery diseases involve circulatory problems in which narrowed arteries reduce blood flow to body organs. For example, coronary artery disease (CAD) is the most common cardiovascular disease, which involves reduction of blood flow to the heart muscle due to build-up of plaque in the arteries of the heart.

Current clinical practices rely on visual assessment of a diseased vessel. For example, angiography is an X-ray based technique used in the examination of arteries, veins and organs to diagnose and treat stenoses (narrowing, usually due to atherosclerosis) and other blood vessel problems. During an angiogram, a catheter is inserted into an artery or vein from an access point and a contrast agent is injected through the catheter to make the blood vessels visible on an X-ray image.

While providing an anatomical overview of a diseased vessel, visual assessment does not provide the functional significance of a blockage, namely, the effect of the blockage on blood flow through the vessel.

Fractional flow reserve (FFR) is a technique used to measure pressure differences across a stenosis to determine the likelihood that the stenosis impedes oxygen delivery to the heart muscle. FFR is defined as the pressure after (distal to) a stenosis relative to the pressure before the stenosis, thus expressing the maximal flow down a vessel in the presence of a stenosis compared to the maximal flow in the hypothetical absence of the stenosis. Some techniques use three dimensional models or reconstructions of vessels from which to calculate functional measurements such as FFR. In some cases, 2D images of vessels, obtained from different angles, are used to construct 3D models of vessels.

Some systems interface with a health professional, displaying the 3D model and calculation results based on the 3D model.

However, reconstructing a full 3D model from images input to the system is a typically slow process which requires heavy use of immediately available memory.

Additionally, existing systems require user input based on which functional measurements are calculated. For example, a health professional is required to mark a location on an image of a vessel, after which calculations are made on the marked location. This necessary interaction with the user taxes the user's resources and means that results cannot be provided in real-time.

Thus, existing systems cannot provide immediate, online, results and have no or limited flexibility to improve results based on new or different images fed into the system on-line.

SUMMARY

Embodiments of the invention provide a fully automated solution to vessel analysis based on image data. A system, according to embodiments of the invention, detects a pathology from an image of a vessel, without requiring user input regarding the location of the vessel or the pathology. The system may then track the pathology throughout a sequence of images of the vessel such that the same pathology can be identified in different images, possibly images captured from different angles.

In one embodiment, there is provided a system for analysis of a vessel (e.g., coronary blood vessel). The system may automatically detect a pathology in a first image of the vessel and attach a virtual mark to the pathology, namely, to the location of the pathology in the first image. The system may detect the pathology in a second image of the vessel, based on the virtual mark and may then provide analysis (e.g., determine an FFR value) of the pathology based on the pathology detected in the first and second images. The analysis may be displayed on the user interface device. For example, an FFR value and/or an indication of the pathology may be displayed on the user interface device.

The first and second images may be each captured at a different angle.

In one embodiment a processor of the system uses computer vision techniques to detect the vessel in the first and second images and to detect the pathology in the first and second images. The processor may then create the virtual mark to indicate the location of the pathology relative to the vessel in the first image and may determine that a pathology detected in the second image, at a same location relative to the vessel, is the same pathology as in the first image.

The ability to identify the same pathology in different images enables an improved automated solution and facilitates user (e.g., health professional) interaction with the system, as detailed herein.

The virtual mark may indicate a location of the pathology within portions of the vessel and/or relative to a structure of the vessel. In some embodiments the processor indexes the pathology based on its location relative to the vessel. The processor of the system may cause, according to a user request for pathologies, an indication of pathology to be displayed based on location of the pathology within the vessel.

According to embodiments of the invention a plurality of pathologies may be detected by the processor, in the first image, and the processor may create a distinct virtual mark for each of the plurality of pathologies. The processor may cause indications of the plurality of pathologies to be displayed on a single display.

A name may be assigned to each of the plurality of pathologies, based on a location of each pathology within the vessel and the processor may cause indications which include the names of the plurality of pathologies to be displayed.

In one embodiment there is provided a flexible system for automated vessel analysis based on images of the vessel. Methods and systems according to embodiments of the invention provide analysis results (such as properties of vessels, diagnoses, functional measurements, etc.), based on images of a vessel. Embodiments of the invention enable to calculate, based on the images of the vessel, a level of accuracy of the results obtainable from those images, and can provide interaction with the user to improve accuracy of analysis.

Embodiments of the invention extract 3D related features from 2D images of a vessel and output an indication of properties of the vessel and/or of functional measurements based on the extracted 3D related features, without using processing time and storage space to construct or use a 3D model of the vessel. Thus, embodiments of the invention provide immediate, substantially real-time results and can improve results, substantially in real-time, based on new or different images provided on-line.

BRIEF DESCRIPTION OF THE FIGURES

The invention will now be described in relation to certain examples and embodiments with reference to the following illustrative figures so that it may be more fully understood. In the drawings.

DETAILED DESCRIPTION

Embodiments of the invention provide methods and systems for automated analysis of vessels from images of the vessels, or portions of the vessels, and display of the analysis results.

Analysis, according to embodiments of the invention, may include information about a property of the vessel, such as geometry related information of a vessel. The analysis may further include functional measurements which may possibly be calculated from one or more property of the vessel. Analysis may also include diagnostic information, such as presence of a pathology, identification of the pathology, location of the pathology, etc. The analysis results, which may include a functional measurement, vessel properties and/or a calculation, diagnosis or other information based on images of the vessel, may be displayed to a user.

A "vessel" may include a tube or canal in which body fluid is contained and conveyed or circulated. Thus, the term vessel may include blood veins or arteries, coronary blood vessels, lymphatics, portions of the gastrointestinal tract, etc.

An image of a vessel may be obtained using suitable imaging techniques, for example, X-ray imaging, ultrasound imaging, Magnetic Resonance imaging (MRI) and others suitable imaging techniques.

"Vessel properties" may include, for example, anatomical characteristics (e.g., shape and/or size of parts of the anatomy) of a vessel and/or of a pathology in the vessel. For example, pathologies may include a narrowing of the vessel (e.g., stenosis or stricture), lesions within the vessel, etc. Thus, vessel properties may include, for example, shape and/or size of vessels and/or parts of vessels, angles of bends in vessels, diameters of vessels (e.g., proximal and distal to a stenosis), minimal lumen diameter (e.g., at the location of a stenosis), lesion length, entrance angle of the stenosis, entrance length, exit angle of the stenosis, exit length, percentage of the diameter blocked by the stenosis, percentage of the area blocked by the stenosis, etc. A pathology or indication of a pathology and/or other diagnosis may be calculated based on these properties.

A "functional measurement" is a measurement of the effect of a pathology on flow through the vessel. Functional measurements may include measurements such as FFR, instant flow reserve (iFR), coronary flow reserve (CFR), quantitative flow ratio (QFR), resting full-cycle ratio (RFR), quantitative coronary analysis (QCA), and more.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "using", "analyzing", "processing," "computing," "calculating," "determining," "detecting", "identifying" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Unless otherwise stated, these terms refer to automatic action of a processor, independent of and without any actions of a human operator.

Figure 1:
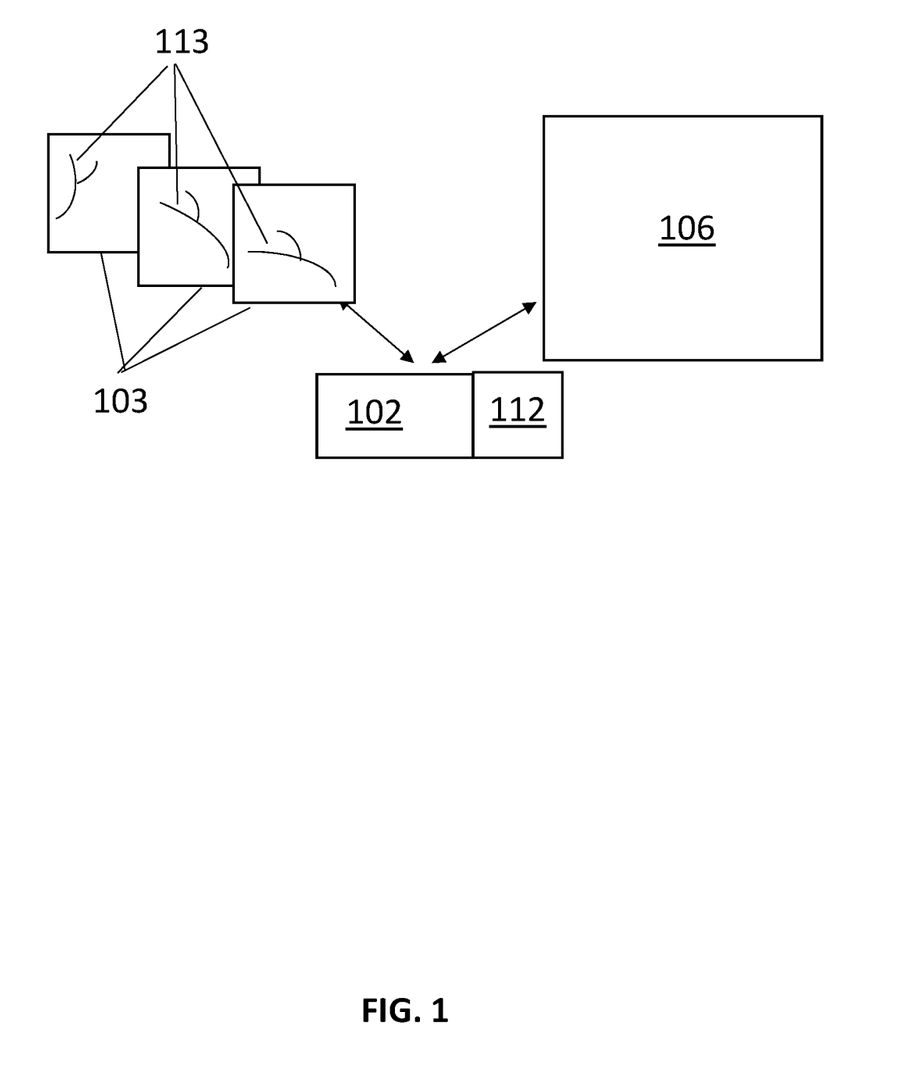
FIG. 1 schematically illustrates a system for analysis of a vessel, according to embodiments of the invention.

In one embodiment, which is schematically illustrated in FIG. 1, a system for analysis of a vessel includes a processor 102 in communication with a user interface device 106. Processor 102 receives one or more images 103 of a vessel 113, each of which may be capturing the vessel 113 from a different angle. Processor 102 then performs analysis on the received image(s) and communicates analysis results and/or instructions or other communications, based on the analysis results, to a user, via the user interface device 106. In some embodiments, user input can be received at processor 102, via user interface device 106.

Vessels 113 may include one or more vessel or portion of a vessel, such as a vein or artery, a branching system of arteries (arterial trees) or other portions and configurations of vessels.

Processor 102 may include, for example, one or more processors and may be a central processing unit (CPU), a graphics processing unit (GPU), a digital signal processor (DSP), a field-programmable gate array (FPGA), a microprocessor, a controller, a chip, a microchip, an integrated circuit (IC), or any other suitable multi-purpose or specific processor or controller. Processor 102 may be locally embedded or remote, e.g., on the cloud.

Processor 102 is typically in communication with a memory unit 112. In one embodiment the memory unit 112 stores executable instructions that, when executed by the processor 102, facilitate performance of operations of the processor 102, as described below. Memory unit 112 may also store image data (which may include data such as pixel values that represent the intensity of reflected light as well partial or full images or videos) of at least part of the images 103.

Memory unit 112 may include, for example, a random access memory (RAM), a dynamic RANI (DRAM), a flash memory, a volatile memory, a non-volatile memory, a cache memory, a buffer, a short term memory unit, a long term memory unit, or other suitable memory units or storage units.

The user interface device 106 may include a display, such as a monitor or screen, for displaying images, instructions and/or notifications to a user (e.g., via graphics, images, text or other content displayed on the monitor). User interface device 106 may also be designed to receive input from a user. For example, user interface device 106 may include or may be in communication with a mechanism for inputting data, such as, a keyboard and/or mouse and/or touch screen, to enable a user to input data.

All or some of the components of the system may be in wired or wireless communication, and may include suitable ports such as USB connectors and/or network hubs.

In one embodiment, processor 102 can determine a property of a vessel from an image of the vessel, typically by applying computer vision techniques such as by applying shape and/or color detection algorithms, object detection algorithms and/or other suitable image analysis algorithms on at least part of one or more of images 103. In some embodiments machine learning models can be used to detect portions of vessels and to determine properties of vessels from images 103. In some embodiments, a pathology and/or a functional measurement for the vessel (e.g., at the location of a pathology) can be determined based on the determined vessel properties.

In some embodiments, a pathology and/or a functional measurement can be determined directly from one (or more) images of the vessel. For example, a pathology and/or a functional measurement can be determined based on a single 2D image of the vessel, without having to determine a property of the vessel.

In some embodiments, properties of vessels and/or functional measurements may be determined by using a combination of structural and temporal data obtained from images of the vessels, e.g., as described below, with reference to FIG. 6.

Typically, each of images 103 captures vessel 113 from a specific angle or point of view.

In one embodiment, determining properties of a vessel may include receiving 2D images of the vessel and extracting 3D related features from the images, without constructing a 3D model of the vessel, for example, without using voxels and/or point clouds or other 3D representations.

The 3D related features are image features, which may be specific structures in the image such as points, edges or objects, or any other information in the image which can be used to determine a property of the vessel from the image. In some embodiments, 3D related features are extracted from images obtained from different views. Features from these images can be used to teach a machine learning model to detect properties of vessels from 2D images. For example, features extracted from 2D images obtained from different views can be combined using a neural network, e.g., a long short term (LS™) neural network, that can compute a feature for each imaged element, integrate the features, keep a representation of the features in memory (hidden state) and update its output as more images are input. Such a neural network may be used for learning properties of vessels and can then be used to determine a property of a vessel and/or a functional measurement from 2D images without having to reconstruct a full 3D representation or use a 3D model of the vessel or use voxels and/or point clouds or other 3D representations.

Extracting 3D related features from a 2D image and determining a vessel property and/or functional measurement from the 3D related features, without constructing a 3D representation and/or without using 3D representations of the vessel, provides a quick process, with minimal cost to accuracy.

In one embodiment, an indication of vessel properties and/or functional measurements that are determined from one or more images of the vessel (e.g., based on extracted 3D related features) can be displayed via user interface device 106.

Medhub's AutoCathFFR™ is, for example, a system for automated calculation of FRR of vessels from images of the vessels. Medhub's AutoCathIFR™ is, for example, a system for automated calculation of an iFR procedure from images of a vessel.

Figure 2:
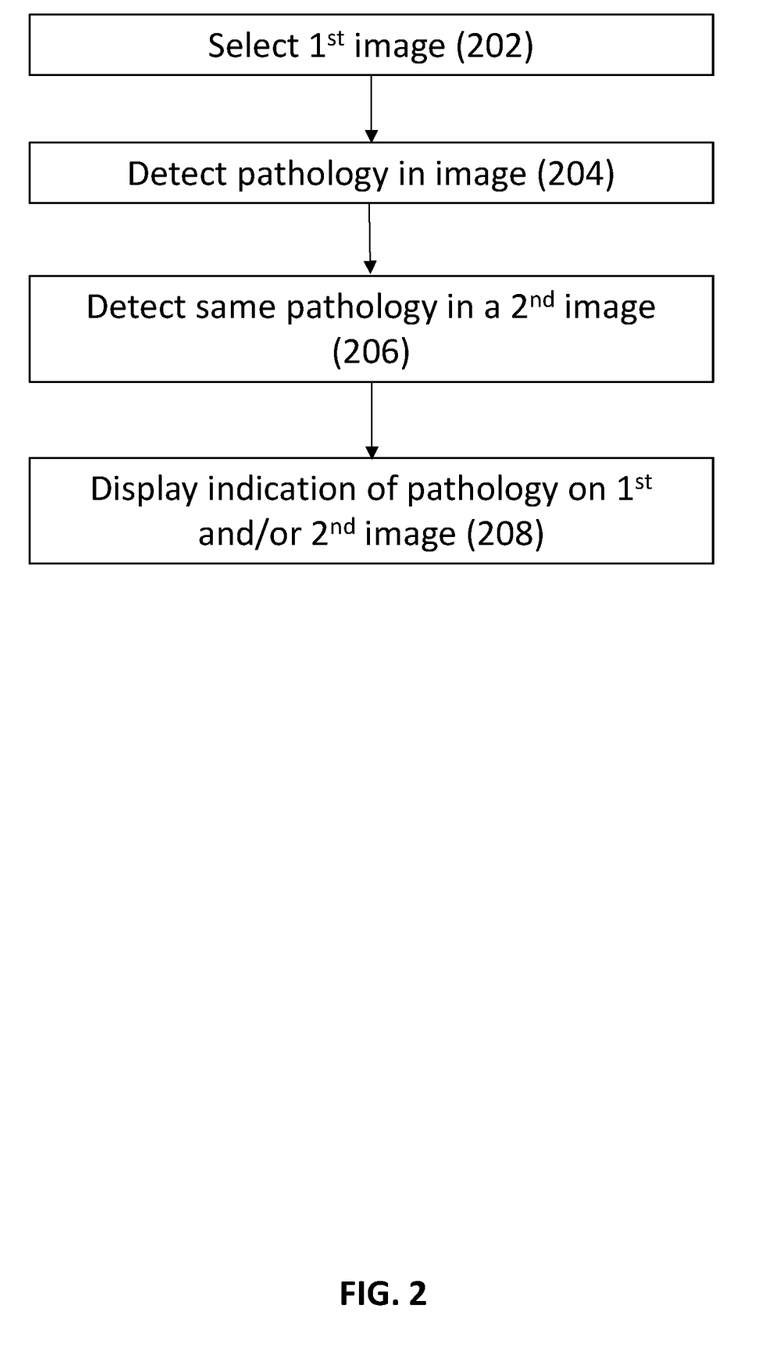
FIG. 2 schematically illustrates a method for analysis of a vessel based on tracking a pathology in between images, according to one embodiment of the invention.

In one embodiment, a system, as described above, includes a processor, e.g., processor 102, that implements a method, which is schematically illustrated in FIG. 2.

A sequence of images of a vessel, such as a video movie of angiogram images, is analyzed by the system. Processor 102 selects, using computer vision techniques, a first image from the sequence of images (step 202) and detects a pathology, such as a stenosis or lesion, in the first image (step 204). Detection of the pathology and/or the location of the pathology is done by using computer vision techniques, without requiring user input regarding a location of the pathology. The processor can automatically detect the pathology in a second image of the vessel (step 206), the second image being captured at an angle different than the first image, and may then cause the first and/or second images of the vessel to be displayed on a user interface device, such as user interface device 106, with an indication of the pathology (step 208).

An indication of a pathology displayed on a user interface device may include, for example, graphics, such as, letters, numerals, symbols, different colors and shapes, etc., that can be superimposed on an image.

Once a pathology is detected in a first image, the pathology may be tracked throughout the images of the sequence (e.g., video), such that the same pathology can be detected in each of the images, even if it's shape or other visual characteristics change in between images.

Figure 3:
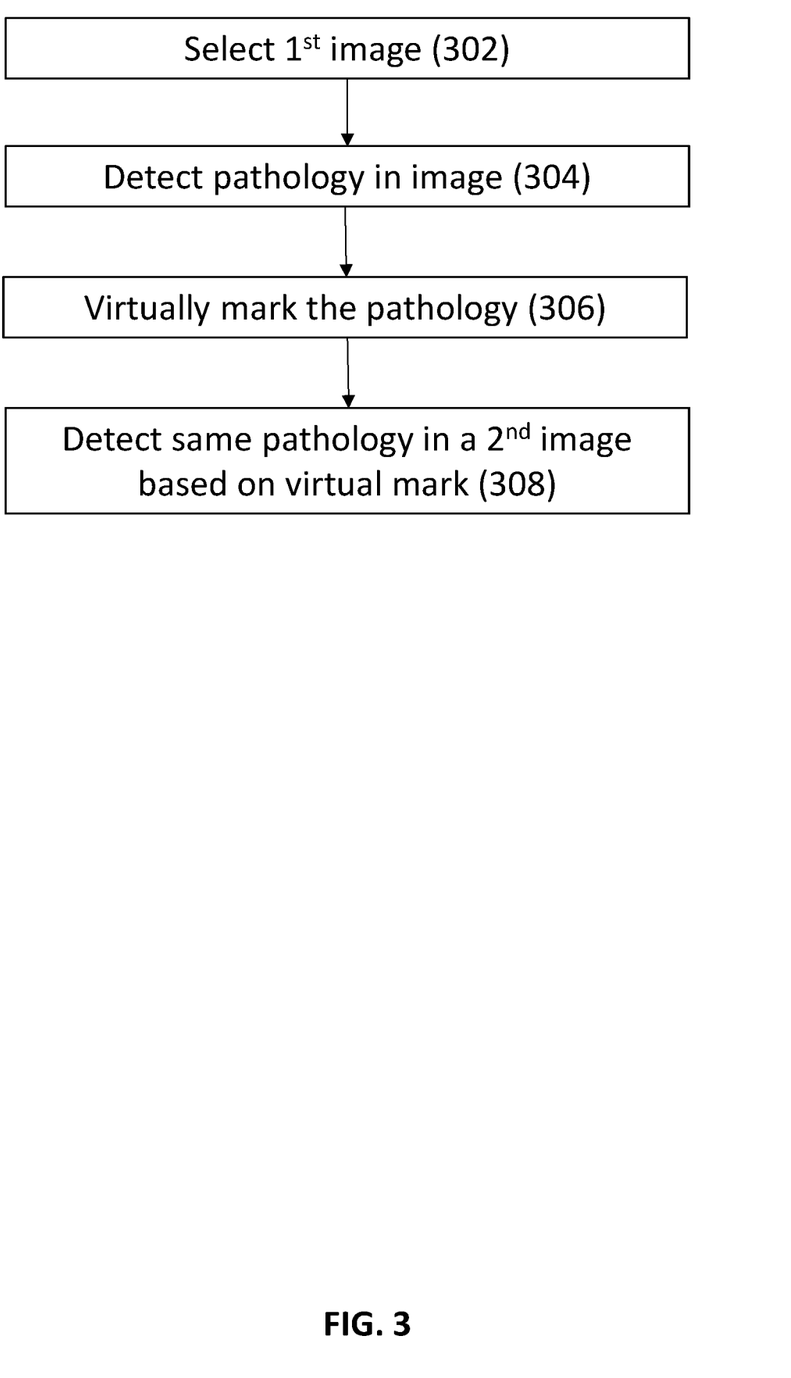
FIG. 3 schematically illustrates a method for analysis of a vessel based on tracking a pathology in between images, according to another embodiment of the invention.

One method of tracking a pathology in between images, is schematically illustrated in FIG. 3. As described above, a first image from a sequence of images is selected (step 302) and a pathology is detected in the first image (step 304). A virtual mark is attached to the pathology by the processor (step 306).

In some embodiments the virtual mark is location based, e.g., based on location of the pathology within portions of the vessel which are automatically detected by the processor 102. In some embodiments, a virtual mark includes the location of the pathology relative to a structure of the vessel. A structure of a vessel can include any visible indication of anatomy of the vessel, such as junctions of vessels and/or specific vessels typically present in patients. Processor 102 may detect the vessel structure in the image by using computer vision techniques, and may then index a detected pathology based on its location relative to the detected vessel structures.

For example, a segmenting algorithm can be used to determine which pixels in the image are part of the pathology and the location of the pathology relative to structures of the vessel can be recorded, e.g., in a lookup table or other type of virtual index. For example, in a first image a stenosis is detected at a specific location (e.g., in the distal left anterior descending artery (LAD)). A stenosis located at the same specific location (distal LAD) in a second image, is determined to be the same stenosis that was detected in the first image. If, for example, more than one stenosis is detected within the distal LAD, each of the stenoses are marked with their relative location to additional structures of the vessel, such as, in relation to a junction of vessels, enabling to distinguish between the stenoses in a second image.

Thus, the processor 102 creates a virtual mark which is specific per pathology, and in a case of multiple pathologies in a single image, distinguishes the multiple pathologies from one another.

The pathology can then be detected in a second image of the vessel (step 308), based on the virtual mark. The processor 102 may then cause display of the indication of the pathology (e.g., as described above) based on the virtual mark. In some embodiments the processor may assign a name to a pathology based on the location of the pathology within the vessel and the indication of pathology can include the name assigned to the pathology, as further demonstrated below.

In some cases, a vessel or group of vessels may include more than one stenosis or other pathology, making detecting a same pathology in different images, more difficult. In some embodiments, a processor detects a plurality of pathologies in the first image and creates a distinct virtual mark for each of the plurality of pathologies. The processor may then cause display of the indication of each of the pathologies based on the virtual mark. In some embodiments the indications are displayed together on a single display.

Thus, a processor according to embodiments of the invention, may determine a functional measurement (e.g., FFR value) of the pathology based on first and second images, e.g., based on the pathology detected in the first and second images, and may display an indication of the functional measurement, e.g., on a user interface device In some embodiments, the processor can determine a level of accuracy of the functional measurement and can calculate a third image required to improve the level of accuracy. The processor can then cause an indication of the third image to be displayed on a user interface, to advise a user which image to add in order to improve accuracy of results.

The first, second and third images are typically each captured at different angles and the indication displayed on the user interface device includes the angle of the third image.

In one embodiment, an optimal frame chosen from a sequence of images of the vessel is used as the first image discussed above.

Figure 4:
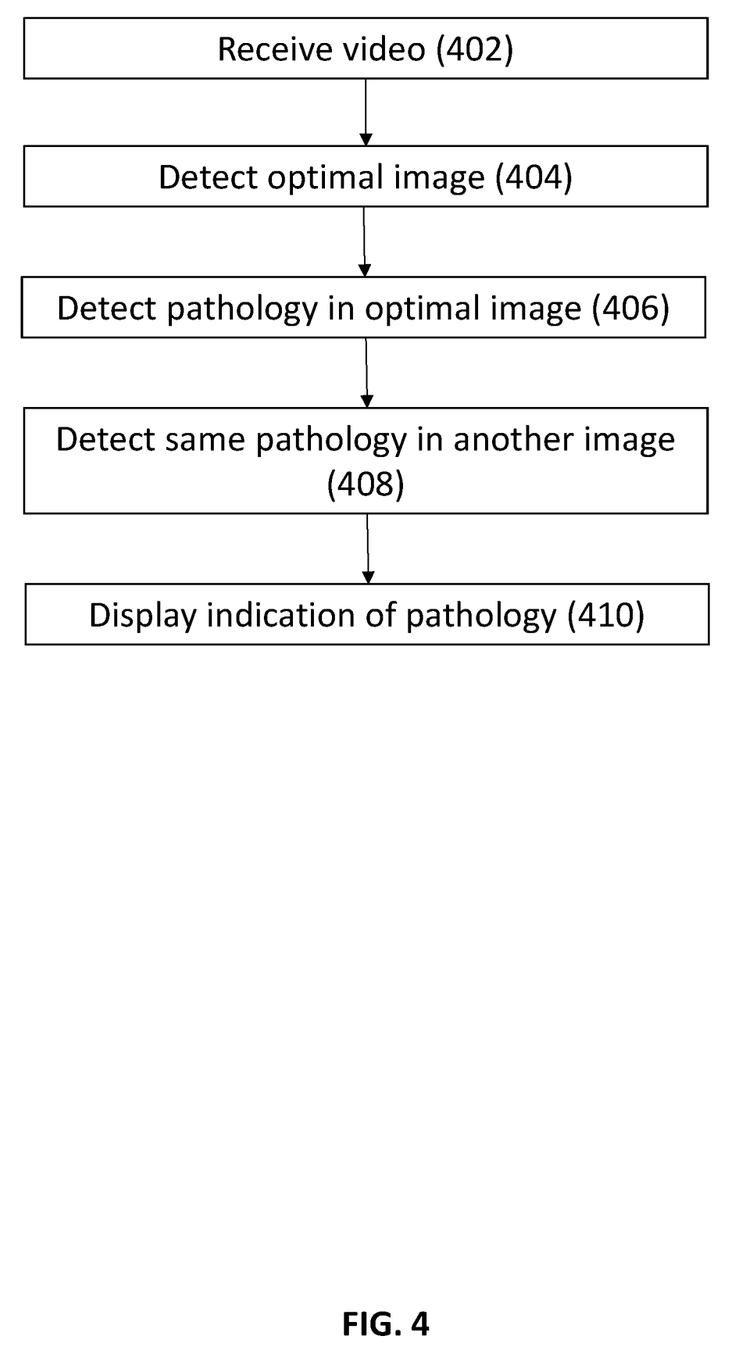
FIG. 4 schematically illustrates a method for analysis of a vessel based on tracking a pathology in between images, according to yet another embodiment of the invention.

In an example, which is schematically illustrated in FIG. 4, a video of angiogram images is received (step 402) and an optimal image is detected (step 404) from the video. A pathology is detected in the optimal image (step 406). The pathology can then be tracked in the images of the sequence and can thus be detected in another frame (step 408) enabling to display an indication of the pathology in all images (step 410).

An optimal image is typically an image showing the most detail. In the case of angiogram images, which include contrast agent injected to a patient to make vessels (e.g., blood vessels) visible on an X-ray image, an optimal image may be an image of a blood vessel showing a large/maximum amount of contrast agent. Thus, an optimal image can be detected by applying image analysis algorithms on the images of the sequence.

In one embodiment an image captured at a time corresponding with maximum heart relaxation is an image showing a maximum amount of contrast agent. Thus, an optimal image may be detected based on capture time of the images compared with, for example, measurements of electrical activity of the heartbeat (e.g., ECG printout) of the patient.

In one embodiment the processor can calculate a value of a functional measurement, such as an FFR value, for each pathology and may cause the value(s) to be displayed.

In some embodiments, processor 102 calculates a level of accuracy of the functional measurement value (e.g., FFR value), based on an angle of capture of the first image, and can cause an indication of the level of accuracy to be displayed on the user interface device 106.

Figure 5:
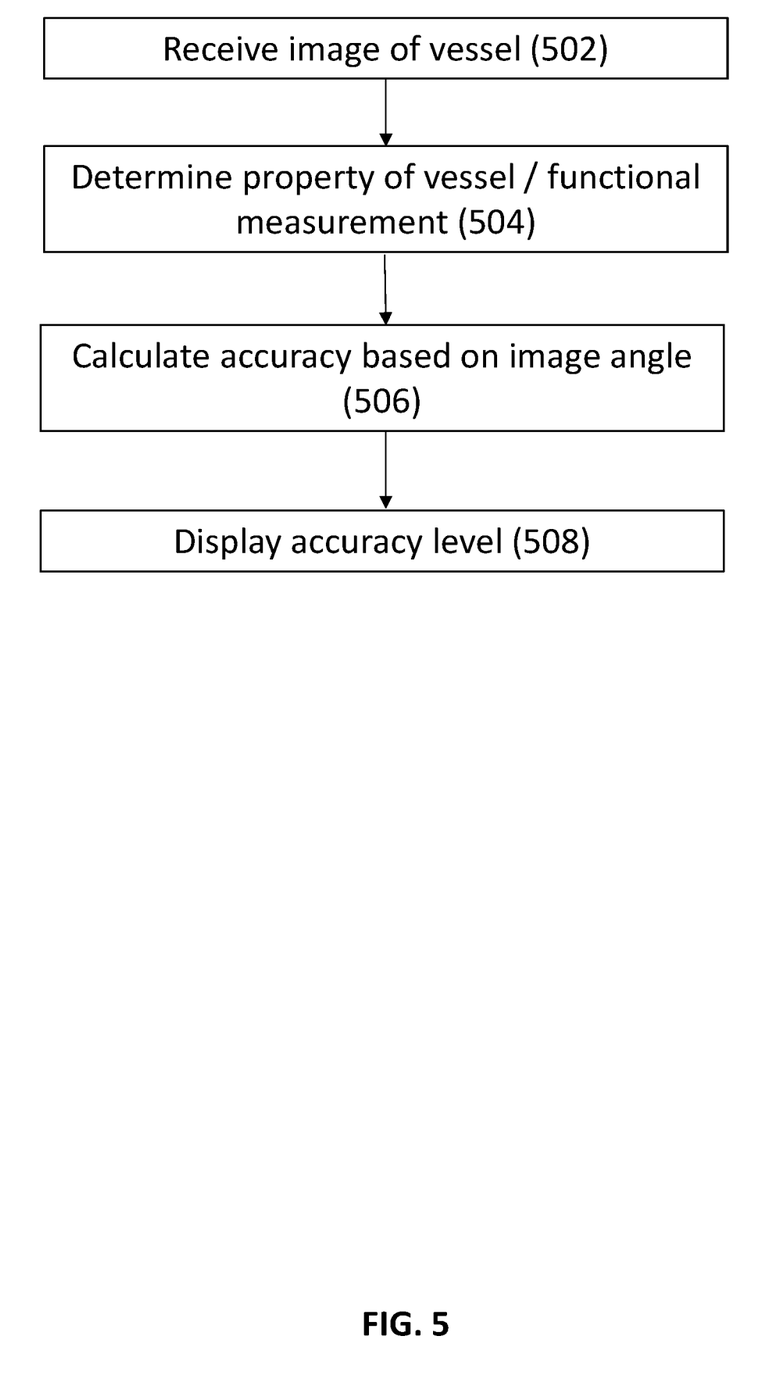
FIG. 5 schematically illustrates a method for analysis of a vessel and interfacing with a user, according to embodiments of the invention.

In one embodiment, which is schematically illustrated in FIG. 5, processor 102 receives an image (e.g., image 103) of a vessel (step 502) and provides an analysis (e.g., determines a property of the vessel and/or a functional measurement) from the image (step 504). For example, processor 102 may apply computer vision algorithms (e.g., as described above) on the received image(s) 103 to determine one or more properties such as, shape and/or size of vessels and/or parts of vessels, angles of bends in vessels, diameters of vessels, minimal lumen diameter, lesion length, entrance angle of the stenosis, entrance length, exit angle of a stenosis, exit length, percentage of the diameter blocked by a stenosis, percentage of the area blocked by a stenosis, etc. Processor 102 may then determine a functional measurement based on the property of the vessel. In other embodiments, processor 102 determines a functional measurement directly from image 103, e.g., by employing a machine learning model to run a regression algorithm to predict a value of a functional measurement (e.g., FFR) from an image of the vessel.

In some embodiments, processor 102 calculates a level of accuracy (also referred to in terms of "margin of error") of the analysis, based on the image(s) 103 (step 506) and may cause an indication of the level of accuracy to be displayed on the user interface device 106 (step 508).

Calculating a level of accuracy can be done, for example, by obtaining a functional measurement for a vessel by using known methods (e.g., physical measurements) and comparing the obtained functional measurement to a functional measurement obtained from an image of the vessel according to embodiments of the invention. A deviation from the measurement obtained by known methods can be used to determine the level of accuracy of the determination based on embodiments of the invention. This can be done for images obtained at all possible angles, thereby creating a map or regression analysis connecting different angle images and/or combination of images to different accuracy levels. This analysis may be performed by carrying out empirical experiments or by using, for example, a predictive model to create a mapping function from an angle of an image to a level of accuracy.

Thus, a processor according to embodiments of the invention may receive an image of the vessel, the image capturing the vessel at an angle, and may calculate a level of accuracy of an analysis (e.g., determination of a property of the vessel and/or of a functional measurement), based on the angle.

Since, according to embodiments of the invention, any image, obtained at any possible angle, can be mapped to a level of accuracy, depending on the required level of accuracy, functional measurements and other analyses, can be obtained based on a single 2D image.

Because processor 102 can detect a specific pathology in different images of a vessel (e.g., images captured from different angles) and can determine a level of accuracy for each pathology based on the different images, processor 102 can calculate which (if any) additional images (captured at which angles) are necessary to adjust, e.g., improve, the accuracy of the analysis.

In one embodiment, the indication of the level of accuracy displayed on the user interface device in step 508, includes instructions or notice for the user (e.g., health professional) regarding how many additional images to add, typically specifying the angle of each additional image, in order to improve the accuracy of the analysis results and lower the margin of error.

In one embodiment processor 102 can provide indication of a single angle of image, which when added to the images already supplied by the user, can provide the most improved accuracy level.

Figure 6:
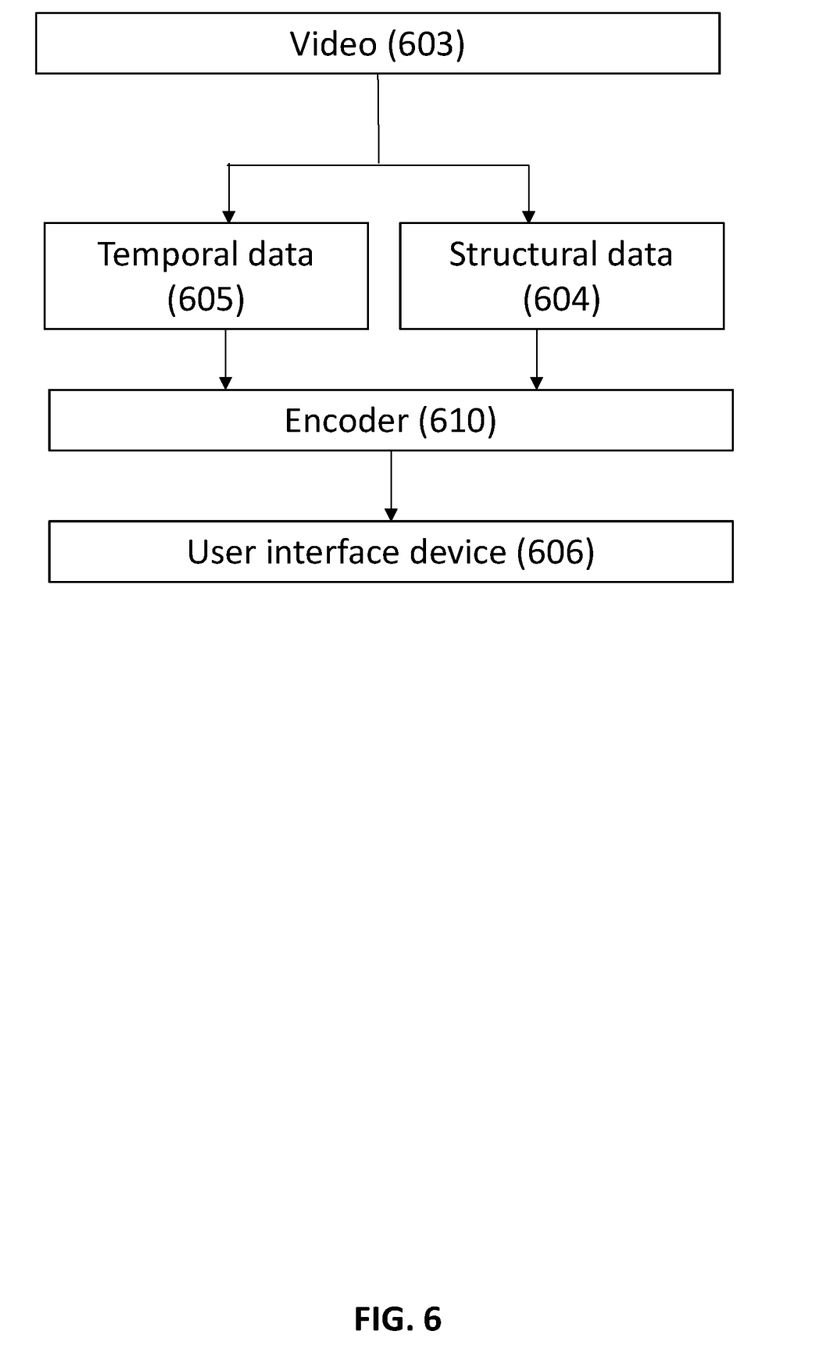
FIG. 6 schematically illustrates a method for analysis of a vessel using temporal and structural data, according to embodiments of the invention.

In one embodiment, which is schematically illustrated in FIG. 6, a sequence of images, e.g., video 603 of angiogram images, is analyzed, e.g., for determining properties of an imaged vessel and/or for calculating a functional measurement for the vessel. A processor obtains structural data 604 of the vessel from at least one image from video 603. The processor also obtains temporal data 605 of the vessel from images of video 603. The structural data 604 and the temporal data 605 are combined and the combined information is analyzed e.g., by encoder 610, to obtain relevant features from which to determine a property of a vessel and/or from which to calculate a functional measurement for the vessel.

In one embodiment, a processor determines a pathology from an image of a vessel and may cause an indication of the pathology to be displayed on the user interface device 606.

In some embodiments, a functional measurement for the vessel can be calculated based on the property of the vessel or based on the relevant features obtained by encoder 610. Indication of the functional measurement can then be displayed on a user interface device 606.

The relevant features calculated by encoder 610 may also be used to determine a property of a vessel, such as a shape or size of a part of a vessel.

In all cases, an indication of the level of accuracy of the displayed analysis (pathology, functional measurement, properties of vessels, etc.) can be calculated and displayed on user interface device 606.

As described above, angiogram images include contrast agent injected to a patient to make vessels (e.g., blood vessels) visible on an X-ray image. Thus, in one embodiment, an image chosen from the angiogram video from which to obtain structural data 604, may be an optimal image, e.g., an image of a blood vessel showing a large/maximum amount of contrast agent.

Temporal data 605 may be obtained from a flow map estimating flow velocity of blood (visible as contrast agent) at points within the vessel. Computing the flow and producing a flow map may be done by applying on the video 603 motion detection algorithms and/or using a neural network trained to estimate motion and output an optical flow map.

Structural data 604 may be obtained by using computer vision techniques, such as by applying a segmenting algorithm on at least one image from the video (e.g., an image showing a maximum amount of contrast agent), to detect in the image a vessel and/or a pathology and/or geometry related or other information.

In some embodiments, portions of a vessel may be detected and a location of a pathology in the vessel can be determined based on the relevant features calculated by encoder 610. The location of the pathology and/or other indications may then be displayed on user interface device 606.

Figure 7:
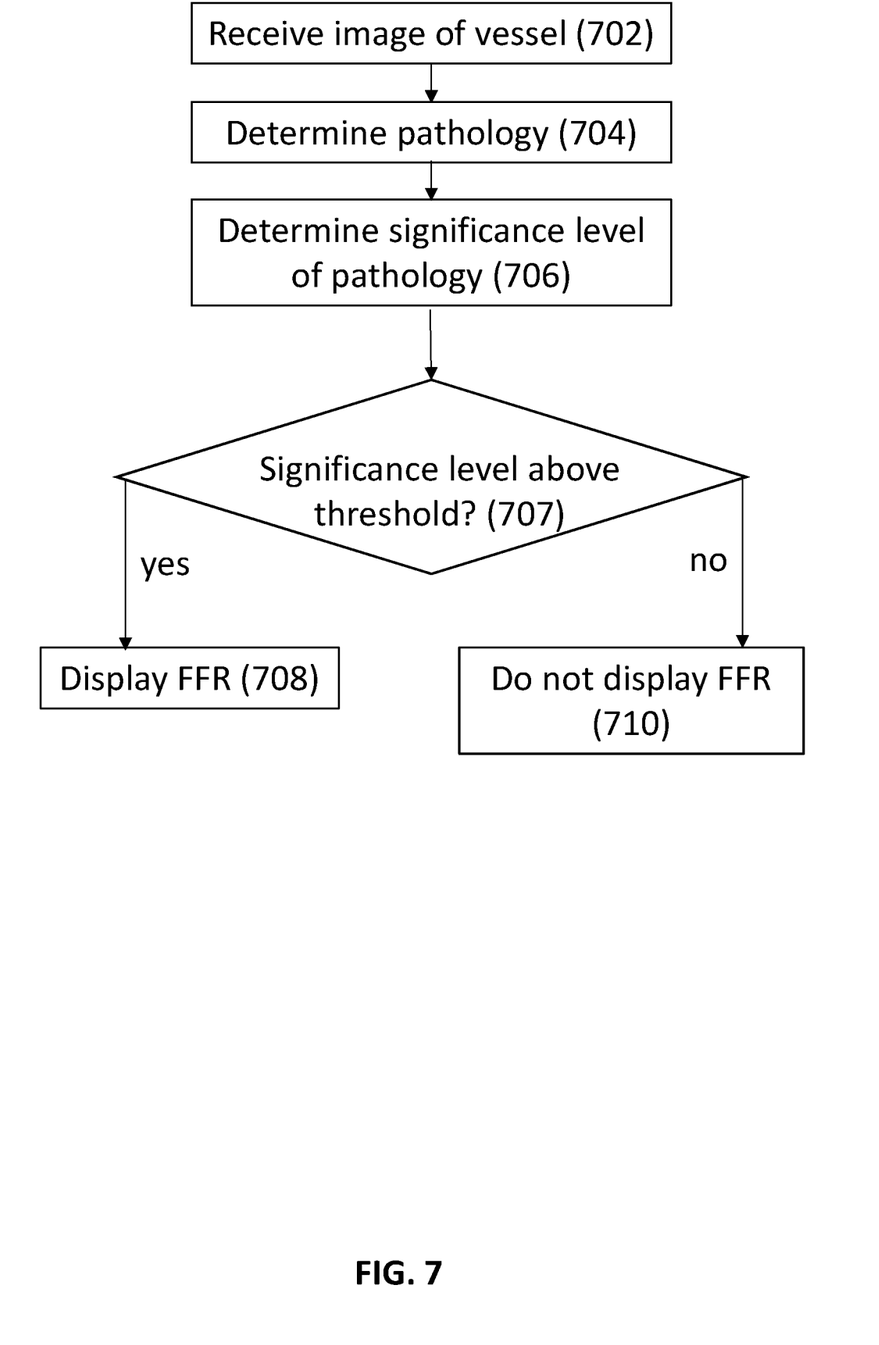
FIG. 7 schematically illustrates a method for determining significance of a pathology and interfacing with a user, according to embodiments of the invention.

In one embodiment, an example of which is schematically illustrated in FIG. 7, a processor, such as processor 102, receives an image of a vessel (step 702) and determines a pathology (e.g., lesion or stenosis) from the image of the vessel (step 704). For example, the pathology may be determined from a property of a vessel and/or from relevant features extracted from images of the vessel, e.g., as described above. The processor may then calculate a level of significance of the pathology (step 706) and may cause an indication of the pathology and/or a functional measurement of the pathology to be displayed based on the level of significance. For example, the level of significance of a pathology may be determined based on parameters of the pathology, such as, size and/or shape of the pathology and/or percentage of the diameter blocked by the pathology, percentage of the area blocked by the pathology, etc.

In one embodiment, if the level of significance is above a threshold, e.g., a predetermined threshold (step 707) the pathology and/or functional measurement related to the pathology will be displayed to a user (708). However, if the level of significance is below the predetermined threshold (step 707) then the pathology and/or functional measurement may not be displayed to the user (step 710). In some embodiments, the pathologies can be rated based on their significance and can be displayed to the user together with their rate, e.g. each pathology can be displayed in a table listing its significance, as described below.

In another embodiment, a level of significance may be calculated by comparing a number of pathologies to each other and/or to a predetermined standard.

Thus, a system for analysis of a vessel includes a processor in communication with a user interface device. The processor determines a pathology of the vessel from an image of the vessel, and calculates a significance level of the pathology and controls a device based on the calculated significance level. For example, the processor can control a user interface device to control its display based on the calculated significance level.

In some embodiments a processor, such as processor 102, can classify a pathology based on one or both of location of the pathology within the vessel and based on a functional measurement, e.g., FFR value. The processor may accept a user request for pathologies based on location within the vessel and/or based on FFR value and may display the pathology according to the classification.

Figure 8A:
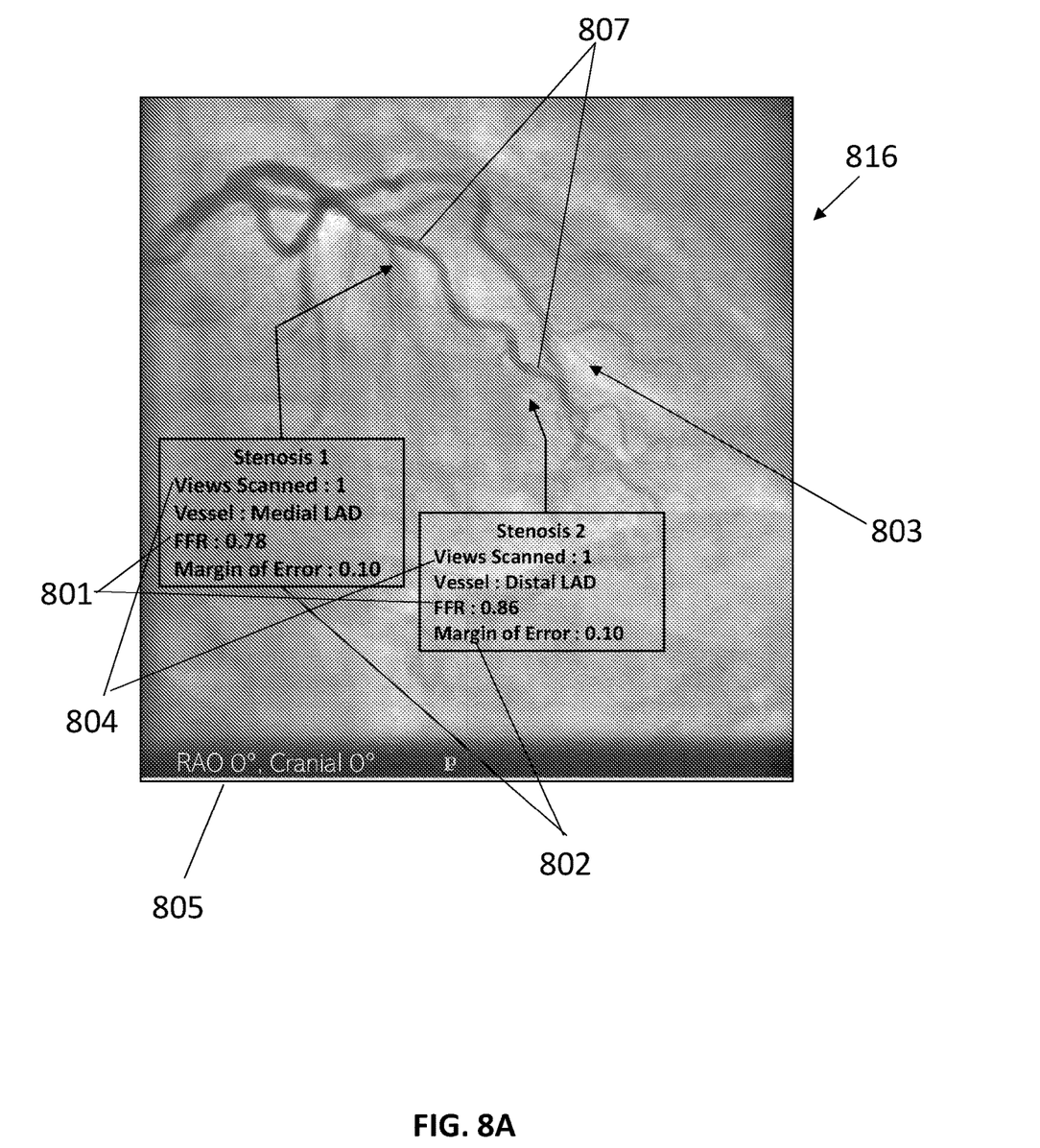
FIGS. 8A and 8B schematically illustrate a user interface according to embodiments of the invention.
Figure 8B:
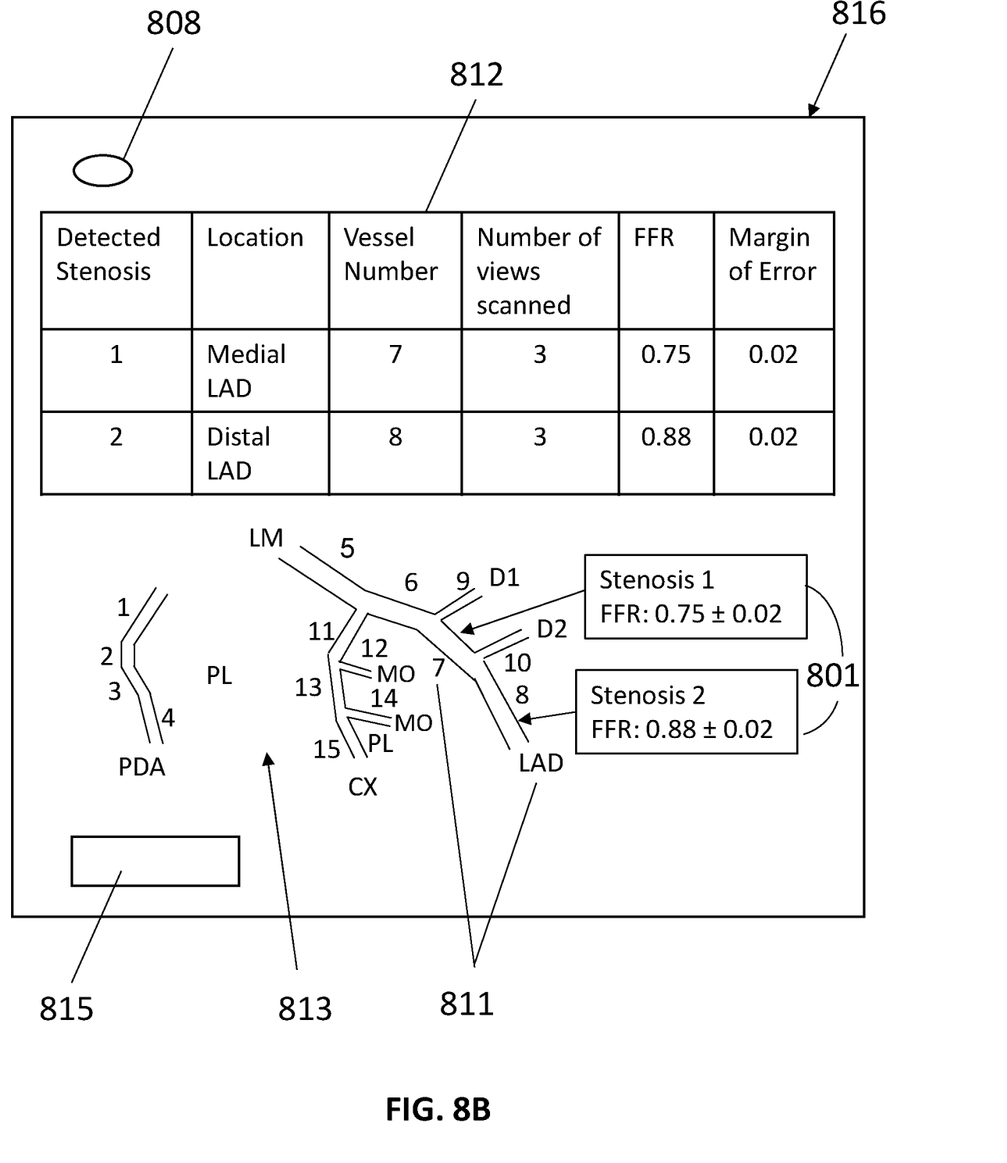

Examples of user interfaces according to embodiments of the invention are schematically illustrated in FIGS. 8A and 8B.

In one embodiment, which is schematically illustrated in FIG. 8A, an image capturing a coronary blood vessel e.g., LAD 803 at a specific angle, is displayed on monitor 816.

In one embodiment, a functional measurement value, FFR 801, is displayed on monitor 816 of a user interface device, together with an indication 804 of the number of images used to calculate the functional measurement FFR 801. In one embodiment, a single image may be used from which a functional measurement is obtained. In some embodiments, even if several images were used to calculate a functional measurement, only one image of LAD 803, which includes the best or most visible features, is displayed on monitor 816.

An indication of one or more pathology, e.g., stenosis 807, can be displayed as graphics superimposed on the displayed image. In some embodiments, the displayed image is a representation of the vessel. For example, the displayed representation may include a combination of images of the vessel, such as a combined image of several images (typically obtained at different angles) or an average image of a few images (obtained at different angles). The angle(s) 805 at which the displayed image(s) were obtained can be indicated on display 816.

In some embodiments, as illustrated in FIG. 8B, the image of the vessel which is displayed on monitor 816 is a graphical illustration 813 of the vessel, rather than an actual image.

Graphics, which may include, for example, letters, numerals, symbols, different colors and shapes, etc., can be displayed superimposed on the representation of the vessel. For example, references 811 can be made to different parts of a LAD and to one or more pathologies. The references 811 can be used to assist a user in locating pathologies, as shown in table 812. For example, the first row of table 812 relates to vessel number 7 in the medial LAD, both of which are shown as references 811 on the graphical illustration 813 of the vessel.

The reference 811 can be assigned by a processor to different vessel portions which were detected by the processor based on computer vision techniques.

In some embodiments, monitor 816 includes a button 808 to enable a user to at least partially hide graphics superimposed on the representation (e.g., image or graphical illustration) of the vessel, so that the user can view the vessel unobstructed by the different graphics. For example, activating button 808 may cause all or specified graphics to fade or become transparent.

The level of accuracy, margin of error 802, of the value of FFR 801 is also displayed on monitor 816. As described above, the margin of error 802 may be known for each image obtained at a known angle. The accuracy level may similarly be known or calculated for combinations of images obtained at different angles. Thus, adding images obtained at different angles may change the level of accuracy of a currently displayed functional measurement. For example, a user (e.g., a health professional) may add images obtained at angles different than angles 805, in order to change the margin of error 802. In some embodiment, monitor 816 includes a window 815 for displaying to the user indication of the angles of additional images that should be input to the system in order to improve the level of accuracy or minimize the margin of error of the analysis results provided by the system.

In one embodiment, processor 102 can classify a pathology based on one or both of location of the pathology within the vessel and its FFR value. In one embodiment the processor may accept a user request for display of pathologies based on location within the vessel and/or based on FFR value.

Because embodiments of the invention enable automatic detection of pathologies in images of vessels and enable marking a location of a pathology in relation to an anatomical structure, pathologies may be identified and marked retroactively, even in images of vessels captured prior to identification of the pathology. Thus, a processor, according to embodiments of the invention, may detect in an image captured prior to detection of the pathology in a first image, the same pathology as in the first image, based on a virtual mark attached to the pathology in the first image. This enables a user to work off-line as well as at the capture time of the images. Working off-line may include retroactively marking pathologies in images as well as classifying images based on a desired parameter and displaying results based on the classification. Additionally, working off-line may include gathering analytics, as described below. For example, a user may request to see all stenoses detected in the medial LAD. The processor may then control a user interface device to display the stenoses according to the requested classification, e.g., to display only images or representations of medial LAD vessels and their respective information (e.g., first row in table 812).

In another example, a user may request to see stenoses having an FFR value above a threshold, in which case processor 102 may cause only stenoses having relevant FFR values to be displayed or indicated on a user interface device.

Embodiments of the invention may be used with images obtained by any suitable imaging methods, e.g., images obtained using quantitative angiography methods, such as, quantitative superficial femoral angiography, ultrasound methods, such as intravascular ultrasound (IVUS), tomography, such as, optical coherence tomography (OCT), and more.

Embodiments of the invention provide systems and methods for obtaining functional measurements such as FFR, the accuracy of which can be improved in real-time, and can be tailored to specific user requirements.

In some embodiments, medical data (such as life expectancy and life longevity) and/or other data (such as age, gender, medical history, etc.) can be input to a system and can be used, together with images of vessels and pathologies in vessels, to create big data. For example, embodiments of the invention enable providing a user with analytics involving functional measurements, such as FFR, gathered from many subjects, e.g., angiograms of all patients examined at a specific facility or network of facilities. Such analytics may include, for example, FFR per gender and per age and FFR per anatomical area and/or per artery. A user interface device according to embodiments of the invention, may provide buttons for user requests for such analytics and/or windows displaying numerical and/or graphical representations of such analytics.

Big data may be used, for example, to predict the risk level of pathologies and possibly best treatment practices per pathology, in the long term. Medhub's AutoCathPred™ is, for example, a system for providing predictions of risky pathologies and best treatment for pathologies, based on big data analysis.

The invention claimed is:

1. A system for analysis of a vessel, the system comprising a processor in communication with a user interface device, the processor configured to:
   i. detect a pathology in a first image of the vessel;
   ii. create a virtual mark which is specific to the pathology in the first image, wherein the virtual mark indicates a location of the pathology relative to a structure of the vessel;
   iii. detect the pathology in a second image of the vessel, based on the virtual mark;
   iv. determine an FFR value of the pathology based on the pathology detected in the first and second images; and
   v. cause an indication of the FFR value to be displayed on the user interface device.

2. The system of claim 1 wherein the vessel comprises a coronary blood vessel.

3. The system of claim 1 wherein the processor is configured to cause an indication of the pathology to be displayed on the user interface device.

4. The system of claim 1 wherein the processor is configured to, using computer vision techniques,
detect the vessel in the first and second images;
detect a pathology in the first and second images;
create the virtual mark to indicate a location of the pathology relative to a structure of the vessel in the first image; and
determine that a pathology detected in the second image, at a same location relative to the structure of the vessel, is the same pathology as in the first image.

5. The system of claim 4 wherein the processor is configured to
index the pathology based on its location relative to the structure of the vessel; and
control a display of the user interface device according to the index.

6. The system of claim 1 wherein the processor is configured to
cause a representation of the vessel to be displayed on the user interface device; and
cause an indication of the pathology to be displayed as graphics superimposed on the representation.

7. The system of claim 1 wherein the processor is configured to
detect a plurality of pathologies in the first image; and
create a distinct virtual mark for each of the plurality of pathologies.

8. The system of claim 7 wherein the processor is configured to cause indications of the plurality of pathologies to be displayed on a single display.

9. The system of claim 7 wherein the processor is configured to assign a name to each of the plurality of pathologies, based on a location of each pathology within the vessel.

10. The system of claim 9 wherein the processor is configured to cause indications which include a name of the vessel to be displayed.

11. The system of claim 1 wherein the first image and second image are each captured at a different angle.

12. The system of claim 11 wherein the first and second images are angiogram images.

13. The system of claim 1 wherein the processor is configured to calculate a level of significance of the pathology and to cause the indication of FFR to be displayed based on the level of significance.

14. The system of claim 1 wherein the processor is to perform steps i-iv retroactively, offline.

15. The system of claim 1 wherein the user interface device is configured to receive a user request for analytics involving FFR and to display the analytics.

16. The system of claim 1 wherein the first and second images are angiogram images.

* * * * *